US006242399B1

(12) United States Patent
Chambers et al.

(10) Patent No.: US 6,242,399 B1
(45) Date of Patent: Jun. 5, 2001

(54) SOAP BAR

(75) Inventors: John George Chambers; Geoffrey Irlam; Bryan Stuart Joy, all of Merseyside (GB)

(73) Assignee: Unilever Home & Personal Care USA, a division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/252,710

(22) Filed: Feb. 18, 1999

(30) Foreign Application Priority Data

Feb. 23, 1998 (GB) ..... 9803771

(51) Int. Cl.[7] ..... A61K 7/50

(52) U.S. Cl. ..... 510/154; 510/152; 510/153; 510/155

(58) Field of Search ..... 510/151, 152, 510/153, 155

(56) References Cited

U.S. PATENT DOCUMENTS

| | | | | |
|---|---|---|---|---|
| 4,310,433 | | 1/1982 | Stiros . | |
| 4,707,496 | | 11/1987 | Simmons . | |
| 4,767,560 | | 8/1988 | Gervasio . | |
| 5,340,492 | * | 8/1994 | Kacher et al. | 252/112 |
| 5,464,554 | | 11/1995 | Gu et al. . | |
| 5,656,579 | * | 8/1997 | Chambers et al. | 510/152 |

FOREIGN PATENT DOCUMENTS

| | | |
|---|---|---|
| 84/04929 | 12/1984 | (WO) . |
| 95/26710 | 10/1995 | (WO) . |
| 97/22684 | 6/1997 | (WO) . |

* cited by examiner

*Primary Examiner*—Necholus Ogden
(74) *Attorney, Agent, or Firm*—Ronald A. Koatz

(57) ABSTRACT

A soap bar comprises:

(A) 30–60% by wt of an alkali metal salt of a fatty acid mixture consisting of:
  (i) 65–90% soap having 1–14 carbon atoms, which includes 2–15% soap having 1–10 carbon atoms, and which further includes 1–10% by wt soap having 1–8 carbon atoms, and
  (ii) 10–35% of soap having greater than fourteen carbon atoms of which 0–25% is unsaturated soap;
(B) 3–35% by wt. fatty acid;
(C) 2–25% by wt. structurant; and
(D) the remainder water.

The product provides higher and creamier lather than other toilet soaps, and also provides a preferred post-use 'draggy' (non-frictional) feel to consumers.

9 Claims, No Drawings

SOAP BAR

The present invention relates to toilet soap bars having improved properties, such as high in-use lathering, low mushing and high creaminess.

Conventional toilet soap bars are the prime personal washing product world-wide. Typically such products comprise a mixture of alkali metal salts, particularly sodium salts of non-lauric fats (such as tallow and palm) and lauric oils (such as coconut oil and palm kernel oil); such alkali metal salts are hereinafter referred to as soap. Usually the ratio of salts of non-laurics to those of lauric oils ranges between 20/80 and 90/10.

In order to meet consumer preference, minor ingredients have often been added to conventional toilet soap bars with the aim of modifying their sensory properties (for example mildness). Typical additives include synthetic surfactants such as sodium cocoyl isethionate, sodium lauryl ether sulphate and a variety of nonionic surfactants.

Unfortunately, the amount of additive required to achieve this aim is usually in excess of 10% by weight of product and, as such, often leads to processing difficulties during manufacture and undesirable in-use properties, for example increased rate of wear due to inclusion of high solubility materials. These products therefore either need special equipment and methods to ensure that adequate processing occurs or need additional additives to correct the undesirable in-use properties. Such special processing requirements and additional additives are usually associated with increased manufacturing costs.

Although bars containing synthetic surfactants are mild and typically provide a 'smooth, wet' after-use skin feel, conventional soap bars provide a 'draggy' (non-frictional) after-use feel which is preferred in certain countries.

It has surprisingly been found that a soap bar with advantageous in-use properties can be prepared, without having to resort to expensive synthetic surfactants, by using a soap blend derived from lauric oils only, for example coconut oil. The resulting bar possesses the advantageous in-use property of being more mild than conventional soap, and in that respect resembles a synthetic surfactant-containing bar, whilst retaining a high volume of creamy lather. However, by avoiding the need for synthetic surfactants, processing difficulties and high mushing are also avoided. Further, the resultant bar also retains the 'draggy' skin feel which is sensorially preferred in certain countries.

U.S. Pat. No. 4,767 560 discloses the use of 'topped' coconut fatty acid in the manufacture of soap. By 'topped' is meant that the short chain fatty acids of the coconut oil have been removed by distillation. The product thus manufactured lacks $C_6$ and $C_8$ soaps, and $C_{10}$ soap is present in an amount less than 2% by wt. of product. The absence of this most soluble component decreases the amount and rate of lathering.

The bars of the present invention differ from those disclosed in U.S. Pat. No. 4,767 560 in that $C_{1-8}$ soaps must be present, and hence rapidly give high amounts of lather.

Thus, according to the present invention a soap bar is provided comprising:

(A) 30–60% by wt of an alkali metal salt of a fatty acid mixture consisting of:
  - (i) 65–90% soap having 1–14 carbon atoms, which includes 2–15% soap having 1–10 carbon atoms, and which further includes 1–10% by wt soap having 1–8 carbon atoms, and
  - (ii) 10–35% of soap having greater than fourteen carbon atoms of which 0–25% is unsaturated soap;

(B) 3–35% by wt. fatty acid;

(C) 2–25% by wt. structurant; and (D) the remainder water.

Component (A) is present in an amount of 30–60% by wt. and preferably 35–55% by wt. Component (A) provides the "non-topped" lauric oil-derived soap content of the composition, and is preferably derived from coconut oil. This component may also comprise soap derived from palm kernel oil.

Fatty acid (B) is preferably present in an amount from 5–30% by wt. Component (B) is preferably saturated $C_{10}$–$C_{24}$ alkyl carboxylic acid and is preferably such that the level of unsaturated fatty acid is less than 20% of the total of fatty acid.

In addition, in component (B), the level of long chain ($\geqq C_{16}$) saturated fatty acids is preferably less than 50% by wt. of total fatty acids.

The fatty acid (B)/soap (A) ratio in the bars of the present invention is typically 0.1 or more.

Structurant (C) is typically present in an amount from 5–20% by wt and may be glycerol. Alternatively, component (C) may be one or more alkaline or alkaline earth salts of short ($\leqq C_8$) chain hydroxy-carboxylic or dicarboxylic acids; or may be a mixture of these with glycerol.

Water (D) is preferably present at 3–15% by wt.

Compositions according to the invention are preferably free of synthetic surfactants, but may in some circumstances contain minor amounts (i.e. 10 wt % or less, preferably 5 wt % or less) of synthetic surfactants. If synthetic surfactants are added, this may typically be to enhance even further the mildness of the composition. If synthetic surfactants are added, suitable synthetic surfactants include anionic surfactants such as for example directly esterified fatty isethionate, nonionic surfactants such as for example alcohol ethoxylates, or amphoteric surfactants, such as for example cocoamidopropyl betaine.

In addition to the ingredients mentioned above, compositions according to the present invention may comprise one or more of the following optional ingredients (examples of which are well known to the person skilled in the art): preservatives, colours, opacifiers, optical brighteners, moisturisers, emollients, germicides, pearlescers, electrolytes, perfumes and other ingredients providing a beneficial effect to the skin.

Examples of such benefit agents include oils (for example silicone oils, mineral oils and synthetic oils such as fatty acid esters) and polymers (such as polyvinylpyrolidone, polyvinylacrylamide, cellulose-based materials, starches and modified starches), as well as any other ingredients well known to provide a beneficial effect to the skin (see the 'International Cosmetic Ingredient Handbook', publ.1997).

Conventional fillers, such as talc, calcite and kaolin may also be included in the composition, for example at 0–30% by wt. of product, preferably at 0–20% by wt.

The products of the invention may be manufactured according to methods known in the art, for example using one of the three process options mentioned below:

I. Glycerol Containing Products:

Fat is saponified in the usual way to form neat soap, and the liberated glycerol is retained in the soap. Free fatty acid is then added to the neat soap, or can be injected into the soap stream prior to drying. Minor ingredients such as opacifiers, colourants and perfume may be added to the dried soap-chips during finishing into bars. The finishing process is conventional by means of mixing, milling, plodding and stamping.

Alternatively, the glycerol can be removed from the neat soap during washing/fitting operations and the required amount of glycerol added prior to drying or during soap finishing.

II. Hydroxy-Carboxylate- or Dicarboxylate-Containing Products:

These materials can be added as aqueous solutions prior to drying, or they can be added in the acid form and used to convert soap to fatty acid. The latter method can be used to form all free fatty acid, or some free fatty acid can also be added as required.

III. Mixed Glycerol/Carboxylate-Containing Products:

These can be manufactured by combining any of the approaches described above in the manufacture of products I and II.

The invention will now be illustrated by the following non-limiting examples:

EXAMPLES

The formulations of the products of the present invention, shown as Examples 1 and 4 in Table 1, were made according to processing option II by premixing sodium lactate solution into neat soap containing free fatty acid, and drying this blend. The minor ingredients were added using a ribbon mixer followed by milling, plodding and stamping into bars.

In addition, the formulations of the present invention shown as Examples 2,3 & 5 were made according to processing option I, by saponifying coconut oil, adding fatty acids and vacuum spray drying the blend. Minor ingredients were added using a ribbon mixer followed by milling, plodding and stamping into bars. Where high levels of talc are present, this is added along with the minor ingredients using a z-blade mixer replacing the ribbon mixer described in the above process.

Billet hardness of formulations 1–5 was comparable to a conventional toilet soap shown as Example 6 consisting of an 80/20 tallow/coconut oil blend at 12% water.

Formulations 1–5 were tested for in-use properties in comparison with this conventional toilet soap.

Firstly, a panel of 20 untrained volunteers qualitatively tested the formulations of the invention, which they judged to have significantly (95% confidence limit) different sensory properties than the conventional soap in terms of ease of lather, copious lather, thick lather, creamy lather, and lather feel.

Secondly, the panel was requested to perform the following quantitative tests:

(i) Lather volume was measured by a handwash method which closely approximates normal consumer use. Each volunteer wore a pair of surgical gloves, and lathered the bar in a standard volume of water at a temperature of 30° C. under a calibrated collecting funnel. The volume of the lather produced was measured in the collecting funnel.

(ii) Lather creaminess was measured as a mean value from panelists estimation.

TABLE 1

| | EXAMPLE | | | | | |
|---|---|---|---|---|---|---|
| | 1 | 2 | 3 | 4 | 5 | 6 |
| Anhydrous CNO* Soap | 67.6 | 74.2 | 60.1 | 66.8 | 73.4 | — |
| 80/20 Tallow/CNO soap blend | — | — | — | — | — | 86.6 |

TABLE 1-continued

| | EXAMPLE | | | | | |
|---|---|---|---|---|---|---|
| | 1 | 2 | 3 | 4 | 5 | 6 |
| Coconut fatty acids | 15.3 | 8.4 | 6.8 | 15.1 | 8.3 | — |
| Glycerol | — | 10.0 | 8.1 | — | 9.9 | — |
| Talc | — | — | 20.0 | — | — | — |
| Sodium Lactate | 10.6 | — | — | 10.5 | — | — |
| Sodium Chloride | — | 0.5 | 0.4 | — | 0.5 | 0.4 |
| perfume | 1.0 | 1.0 | 1.0 | 1.5 | 1.0 | 1.0 |
| water | 5.5 | 5.9 | 3.6 | 6.1 | 6.9 | 12 |
| Lather volume | 81 | 82 | 81 | 79 | 83 | 37 |
| Lather cream | 1.17 | 1.64 | 1.65 | 1.55 | 1.6 | 0.74 |

*CNO = Coconut oil

As can be seen from the above results, the bars of the present invention give a higher volume of creamier lather than conventional toilet soap.

Further, they also provide the unique sensory property of a ‘draggy’ after-use feel, which is preferred by consumers in certain countries. The bars of the present invention also have lower pH than conventional toilet soap, and are therefore less irritating to skin.

What is claimed is:

1. A soap bar comprising:

(A) 30–60% by wt. of an alkali metal salt of a fatty acid mixture consisting of:

(i) 65–90% soap having 1–14 carbon atoms, which includes 2–15% soap having 1–10 carbon atoms, and which further includes 1–10% by wt. soap having 1–8 carbon atoms, and (ii) 10–35% of soap having greater than fourteen carbon atoms of which 0–25% is unsaturated soap;

(B) 3–35% by wt. fatty acid;

(C) 2–25% by wt. of a structurant selected from the group consisting of glycerol and/or one or more alkaline or alkaline earth salts of hydroxy carboxylic or dicarboxylic acid having chain length of $C_8$ or less; and (D) the remainder water;

wherein the composition is absent synthetic surfactant.

2. A soap bar according to claim 1, wherein component (A) is present in an amount from 35–55% by wt.

3. A soap bar according to claim 1, wherein component (B) is present in an amount from 5–30% by wt.

4. A soap bar according to claim 1, wherein component (C) is present in an amount from 5–20% by wt.

5. A soap bar according to claim 1, wherein component (D) is present in an amount from 3–15% by wt.

6. A soap bar according to claim 1, wherein the fatty acids of component (B) are saturated $C_{10}$–$C_{24}$ alkyl carboxylates.

7. A soap bar according to claim 1, wherein in component (B) the level of unsaturated fatty acids is less than 20% of total fatty acids.

8. A soap bar according to claim 1, wherein in component (B) the level of saturated fatty acids having a chain length of $C_{16}$ or greater is less than 50% of total fatty acids.

9. A soap bar according to claim 1, wherein in component (B) the fatty acid/soap ratio is 0.1. or more.

* * * * *